United States Patent [19]

Tessier et al.

[11] Patent Number: 4,537,897
[45] Date of Patent: Aug. 27, 1985

[54] 3-(1,2-PROPADIENYL)-CYCLOPROPANE-CARBOXYLATES

[75] Inventors: Jean Tessier, Vincennes; Jean-Pierre Demoute, Montreuil-Sous-Bois; Joseph Cadiergue, Aulnay-Sous-Bois, all of France

[73] Assignee: Roussel Uclaf, Paris, France

[21] Appl. No.: 532,825

[22] Filed: Sep. 15, 1983

[30] Foreign Application Priority Data

Sep. 29, 1982 [FR] France .................. 82 16372

[51] Int. Cl.³ .................. A01N 53/00; C07D 213/68; C07C 69/743; C07C 69/747
[52] U.S. Cl. .................. 514/351; 514/389; 514/417; 514/425; 514/443; 514/445; 514/461; 514/471; 514/521; 514/531; 546/300; 548/312; 548/477; 548/479; 548/513; 548/546; 548/547; 549/479; 549/499; 560/124; 562/506; 260/465 B
[58] Field of Search .............. 549/479, 499; 560/124; 562/506; 260/465 B; 546/300; 548/312, 477, 479, 513, 546, 547; 424/263, 274, 273 R, 285, 305, 304, 275, 306

[56] References Cited

U.S. PATENT DOCUMENTS 4,315,943 2/1982 Martel et al. .................. 424/304

Primary Examiner—Henry R. Jiles
Assistant Examiner—Dale A. Bjorkman
Attorney, Agent, or Firm—Bierman, Peroff & Muserlian

[57] ABSTRACT

Novel 3-(1,2-propadienyl)-cyclopropane-carboxylates of the formula

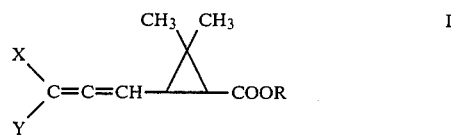

wherein R is alcohol used in pyrethrinoid synthesis, X and Y are both hydrogen or individually halogen or X is hydrogen or halogen and Y is alkyl of 1 to 18 carbon atoms or halogen or X is hydrogen or halogen or alkyl of 1 to 18 carbon atoms and Y is —COOR' or —CN or

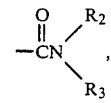

R' is alkyl of 1 to 18 carbon atoms, $R_2$ and $R_3$ are individually hydrogen or alkyl of 1 to 18 carbon atoms or $R_2$ and $R_3$ together with the nitrogen atom form a heterocycle having pesticidal properties.

28 Claims, No Drawings

3-(1,2-PROPADIENYL)-CYCLOPROPANE-CARBOXYLATES

STATE OF THE ART

U.S. Pat. No. 4,315,943 describes 2,2-dimethylcyclopropane-carboxylates but with an allenic side chain in the 3-position.

OBJECTS OF THE INVENTION

It is an object of the invention to provide the novel compounds of formula I and novel intermediates and novel process for their preparation.

It is another object of the invention to provide novel pesticidal compositions and a novel method of combatting pests.

These and other objects and advantages of the invention will become obvious from the following detailed description.

THE INVENTION

The novel compounds of the invention are 3-(1,2-propadienyl)-cyclopropane-carboxylates of the formula $$\underset{Y}{\overset{X}{\diagdown}}C=C=CH-\underset{}{\overset{CH_3\ CH_3}{\triangle}}-COOR \qquad I$$

wherein R is alcohol used in pyrethrinoid synthesis, X and Y are both hydrogen or individually halogen or X is hydrogen or halogen and Y is alkyl of 1 to 18 carbon atoms or halogen or X is hydrogen or halogen or alkyl of 1 to 18 carbon atoms and Y is —COOR' or —CN or $$-\overset{O}{\overset{\|}{C}}N\overset{R_2}{\underset{R_3}{\diagdown}},$$

R' is alkyl of 1 to 18 carbon atoms, $R_2$ and $R_3$ are individually hydrogen or alkyl of 1 to 18 carbon atoms or $R_2$ and $R_3$ together with the nitrogen atom form a heterocycle.

When X and Y are halogen, they are preferably chlorine, bromine or fluorine and when X, Y or R' are alkyl, they are preferably methyl, ethyl, n-propyl, isopropyl, n-butyl, isobutyl, tert.-butyl or n-pentyl, when Y is $$-\overset{O}{\overset{\|}{C}}N\overset{R_2}{\underset{R_3}{\diagdown}},$$

$R_2$ and $R_3$ are preferably alkyl as discussed above for X and Y. Among the preferred compounds of formula I are those wherein X and Y are both hydrogen.

Other preferred compounds of formula I are those wherein R is selected from the group consisting of (1) alkyl of 1 to 18 carbon atoms, (2) benzyl optionally substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy and halogens, $$\underset{R_1}{\overset{-CH_2}{\diagup}}\underset{O}{\diagdown}\underset{}{\diagup}CH_2R'_2 \qquad (3)$$

wherein $R_1$ is selected from the group consisting of hydrogen and methyl and $R'_2$ is selected from the group consisting of —C≡CH and monocyclic aryl, $$\text{(4)}$$

wherein a is selected from the the group consisting of hydrogen and methyl and $R'_3$ is an aliphatic group of 2 to 6 carbon atoms containing at least one carbon-carbon unsaturation, $$\text{(5)}$$

wherein a and $R'_3$ have the above definition and $R_1'$ and $R_2''$ are individually selected from the group consisting of hydrogen, halogen, alkyl of 1 to 6 carbon atoms, aryl of 6 to 10 carbon atoms, cyano and alkoxy carbonyl of 2 to 5 carbon atoms, $$\text{(6)}$$

wherein B is selected from the group consisting of —CH$_2$—, $$-\overset{O}{\overset{\|}{C}}-,$$

—O— and —S—, $R_4$ is selected from the group consisting of hydrogen, C≡N, —CH$_3$, —CONH$_2$, —CSNH$_2$ and —C≡CH, n is an integer from 0, 1 or 2 and $R_5$ is selected from the group consisting of halogen and —CH$_3$ $$\text{(7)}$$

$$\text{(8)}$$

wherein $R_6$, $R_7$, $R_8$ and $R_9$ are selected from the group consisting of hydrogen, chlorine and methyl and S/I symbolizes an aromatic ring or dihydro, tetrahydro or hexahydro ring, (9) (succinimido or maleimido) —CH$_2$—

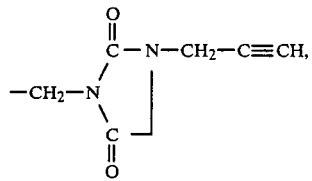
(10)

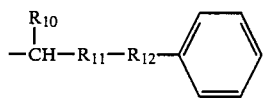
(11)

wherein $R_{10}$ is selected from the group consisting of hydrogen and —CN, $R_{12}$ is selected from the group consisting of —CH$_2$— and —O— and $R_{11}$ is selected from the group consisting of thiazolyl and thiadiazolyl with the bond to

being in any one of the positions, $R_{12}$ being bonded to $R_{11}$ by the carbon atom included between a sulfur atom and a nitrogen atom,

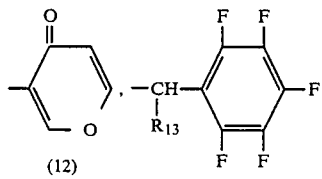
(12)  (13)

wherein $R_{13}$ is selected from the group consisting of hydrogen and —CN,

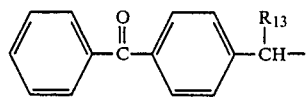
(14)

wherein $R_{13}$ has the above definition

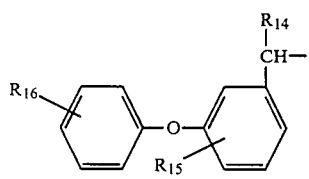
(15)

wherein $R_{14}$ is selected from the group consisting of hydrogen, methyl, ethynyl and —CN and $R_{15}$ and $R_{16}$ are individually selected from the group consisting of hydrogen, bromine and fluorine and

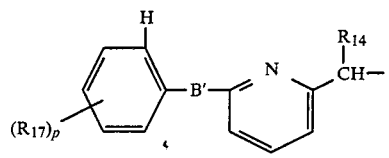
(16)

wherein $R_{14}$ has the above definition, p is 0, 1 or 2, each $R_{17}$ is selected from the group consisting of alkyl of 1 to 4 carbon atoms, alkoxy of 1 to 4 carbon atoms, alkylthio of 1 to 4 carbon atoms, alkylsulfonyl of 1 to 4 carbon atoms, —CF$_3$, 3,4-methylenedioxy, chlorine, bromine and fluorine, B' is selected from the group consisting of —O— and —S—.

An example of $R_2'$ as monocyclic aryl is 5-benzyl-3-furylmethyl and examples of $R_3'$ are —CH$_2$—CH=CH$_2$, —CH$_2$—CH=CH—CH$_3$, —CH$_2$—CH=CH—CH$_2$—CH$_3$, —CH$_2$—CH=CH—CH=CH$_2$ and —CH$_2$—C≡CH. Examples of substituent (6) are 3-phenoxy-benzyl, α-cyano-3-phenoxy-benzyl, α-ethynyl-3-phenoxy-benzyl, 3-benzoyl-benzyl, 1-(3-phenoxyphenyl)-ethyl and α-thioamido-3-phenoxy-benzyl.

Examples of R are alkyl such as methyl, ethyl, n-propyl, isopropyl, isobutyl, tert.-butyl and n-butyl, benzyl optionally substituted with at least one alkyl such as methyl or ethyl; benzyl optionally substituted with at least one alkenyl such as vinyl, allyl, 2-methylallyl and isobutenyl; and benzyl substituted with an alkadienyl of 4 to 6 carbon atoms, benzyl substituted with at least one alkenyloxy such as vinyloxy, allyloxy, 2-methylallyloxy and isobutenyloxy; and benzyl substituted with at least one halogen such as chlorine, bromine and fluorine.

When R is

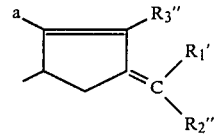

$R_3'$ is preferably selected from the group consisting of —CH$_2$—CH=CH$_2$, —CH$_2$—CH=CH—CH$_3$, —CH$_2$—CH=CH—CH=CH$_2$ and —CH$_2$—CH=CH—CH$_2$—CH$_3$ and when $R_1'$ and/or $R_2''$ are halogen, they are preferably chlorine, bromine or fluorine. When $R_1'$ and/or $R_2''$ are alkyl, they are preferably methyl, ethyl, n-propyl or n-butyl and when they are aryl, they are preferably phenyl. Wherein $R_1'$ and/or $R_2''$ are alkoxycarbonyl, they are methoxycarbonyl or ethoxycarbonyl preferably.

When R is

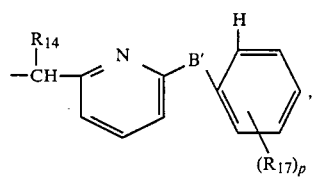

and $R_{17}$ is preferably selected from the group consisting of alkyl, alkoxy, alkylthio or alkylsulfonyl, $R_{17}$ is preferably methyl, ethyl, ethoxy, methoxy, methylthio, ethylthio, methylsulfonyl or ethylsulfonyl.

Among the preferred compounds of formula I are those wherein R is selected from the group consisting of α-cyano-3-phenoxy-benzyl, α-cyano-3-phenoxy-4-fluoro-benzyl, 2-methyl-3-allyl-4-oxo-2-cyclopenten-1-yl and 5-benzyl-3-furyl-methyl.

The process of the invention for the preparation of the compounds of formula I comprises reacting an acid of the formula

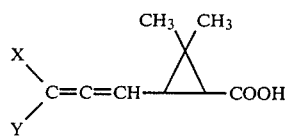

or a functional derivative thereof wherein X and Y and the above definition with an alcohol of the formula R—OH wherein R has the above definition or a functional derivative thereof.

In a preferred mode of the process of the invention, the esterification of the acid and the alcohol is effected in the presence of 4-dimethylamino-pyridine and dicyclohexylcarbodiimide.

When X and Y in the compounds of formula I are both hydrogen, 1R,trans or 1R,cis 2,2-dimethyl-3-(1,2-propadienyl)-cyclopropane-carboxylic acid (compound II when X and Y are hydrogen) may be prepared by reacting an alkyl (1R,trans) or (1R,cis) 2,2-dimethyl-3-(2,2-dibromovinyl)-cyclopropane-carboxylate wherein alkyl has 1 to 8 carbon atoms with butyllithium to obtain the corresponding alkyl (1R,trans) or (1R,cis) 2,2-dimethyl-3-ethynyl-cyclopropane-carboxylate, reacting the latter with diisopropylamine, formaldehyde and cuprous bromide to obtain alkyl (1R,trans) or (1R,cis) 2,2-dimethyl-3-(1,2-propadienyl)-cyclopropane-carboxylate and saponifying the latter with an aqueous basic agent to obtain the desired starting carboxylic acid.

The compounds of formula I wherein Y is hydrogen and X is chlorine or bromine may be prepared by the following reaction scheme:

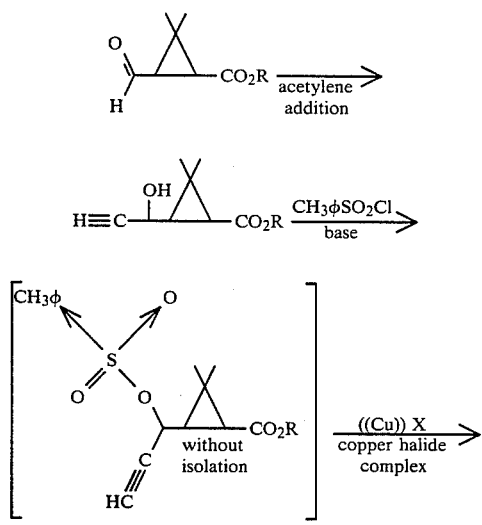

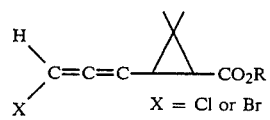

The compounds of formula I wherein X is hydrogen, halogen or alkyl of 1 to 18 carbon atoms and Y is —COOR' and R' is alkyl of 1 to 18 carbon atoms may be prepared by the following reaction scheme:

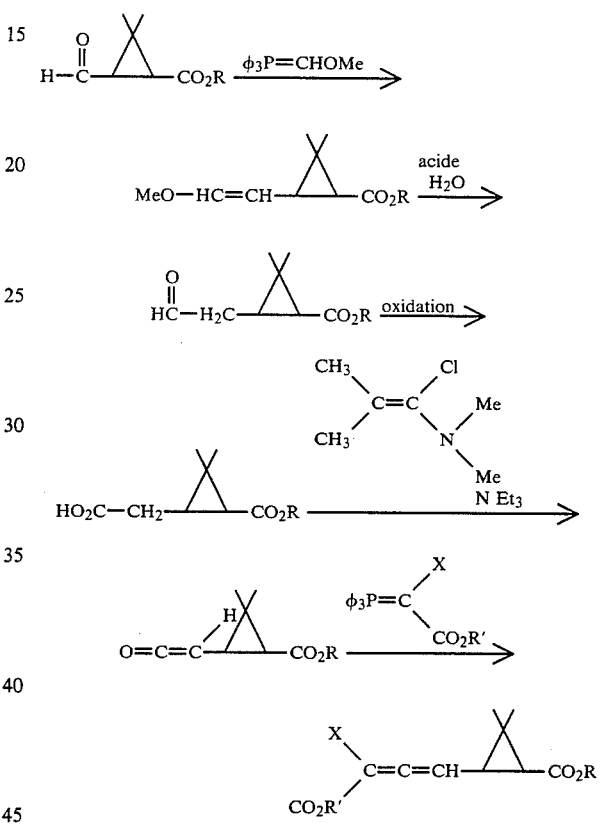

Various process for the preparation of the compounds of formula I are illustrated in the Examples.

The compounds of formula II, and especially where X and Y are hydrogen, are novel intermediates and are a portion of the invention as well.

The novel pesticidal compositions of the invention are comprised of a pesticidally effective amount of at least one compound of formula I and an inert carrier. The compositions are useful to combat pests such as parasites of vegetables and of warm-blooded animals as well as parasites of premises and are particularly useful to combat insects, nematodes and parasitic acariens which attack warm-blooded animals and vegetables.

The compositions of the invention are particularly useful to combat insects in the agricultural field, for example, to control aphides and larvae of lepidoptera and coleoptera and are usually used at a dose of 10 to 300 g of the compounds of formula I per hectare. The compositions are also useful to combat insects in the premises for example to combat flies, mosquitoes and beetles.

The insecticidal compositions of the invention are particularly preferred and may contain 0.005 to 10% by weight of the active ingredient.

In an advantageous operation for use in premises, the compositions are in the form of fumigants. These compositions advantageously have for their inactive portion a combustible serpentine or coil base or an incombustible fibrous substrate. In the latter case, the fumigant obtained after incorporation of the active ingredient of formula I is placed in a heating apparatus such as an electromosquitoe destroyer. The usual active dose in this case is 0.03 to 95% by weight, preferably.

In the case of a serpentine insecticide, the inert support may be made, for example, of pyrethrum marc, Tabu powder (or *Machilus Thumbergii* leaf powder), powder of pyrethrum stems, cedar needle powder, sawdust such as pine sawdust starch and powder of coconut shells. The active dose in this case is preferably 0.03 to 1% by weight.

The compositions of the invention for premises use may be prepared as a spraying oil containing the active ingredient and the oil may soak the wick of a lamp which is then subjected to combustion. The concentration of the compound of formula I in the oil is preferably 0.03 to 95% by weight.

The compositions of the invention are also useful to combat acariens and nematode parasites of vegetables containing at least one compound of formula I as the active ingredient and they may be in the form of powders, granules, suspensions, emulsions or solutions.

For acaricide use, the compositions are preferably wettable powders for foliar spraying containing 1 to 80% of the active ingredients or liquids for foliar spraying containing 1 to 500 g/l of the active ingredient. Also useful are powders for foliar powdering containing 0.05 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

The compositions may also contain one or more other pesticidal agents. The compositions may be in the form of powders, granules, suspensions, emulsions, solutions, aerosol solutions, combustible bands, baits and other preparations classically used for compounds of this type.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The products of formula I have the advantages of being very photostable and not being toxic to mammals. The various properties of the compounds of formula I correspond perfectly to those required for modern agrochemical use permitting the protection of crops without damage to the environment.

The compositions of the invention are also useful to combat acarien parasites of warm-blooded animals such as ticks, especially ticks of Boophilus species, Hyalomnia species, Amblyomnia species and Rhipicephalus species and to combat all sorts of scabies such as sarcoptic scabies, psoroptic scabies and chorioptic scabies. They can also be useful to combat lice and helminthes. The invention also includes compositions intended to combat parasites of warm-blooded animals, especially ticks and gales, containing at least one compound of formula I.

The said medicaments may be administered externally by vaporization, by powdering, by painting or by bathing. For veterinary usage, the compositions may also be administered by painting the dorsal spine by the "pour on" method as well as being administered digestively or parenterally.

When the compositions are to be used to combat parasitic acariens of animals, the active compounds of formula I are very often incorporated into alimentary compositions in association with a nutritive mixture adapted to the animal to be fed. The nutritive mixture will vary depending upon the species of animal but usually contains cereals, sugars and grains, soybean press cake, peanuts and turnsole, meal of animal origin such as fish meal, synthetic amino acids, mineral salts, vitamins and antioxidants.

Another feature of the invention are insecticidal, acaricidal or nematocidal compositions containing as an active ingredient at least one compound of formula I and as a second active ingredient at least one pyrethrinoid ester selected from the group consisting of esters of allethrolone, of 3,4,5,6-tetrahydrophthalimidomethyl alcohol, of 5-benzoyl-3-furyl-methyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene methyl)-cyclopropane-1-carboxylic acids, esters of 3-phenoxy-benzyl alcohol and α-cyano-3-phenoxy-benzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)cyclopropane-1-carboxylic acids, esters of 3-phenoxy-benzyl alcohol with 2-p-chlorophenyl-2-isopropyl-acetic acids, esters of allethrolone, 3,4,5,6-tetrahydrophthalimidomethyl alcohol, 5-benzyl-3-furyl-methyl alcohol, 3-phenoxy-benzyl alcohol or α-cyano-3-phenoxy-benzyl alcohols with 2,2-dimethyl-3-(1,2,2,2-tetrahaloethyl)-cyclopropane-1-carboxylic acids where halo is fluorine, chlorine or bromine wherein the compounds of formula I and the above pyrethrinoid esters are in all possible stereoisomer forms.

The latter associated compositions of the invention are of particular interest for combatting by the polyvalence of their action, a large range of parasites.

To increase the biological activity of the compositions of the invention, classical synergists may be incorporated therein such as 1-(2,5,8-trioxadodecyl)-2-propyl-4,5-methylenedioxy-benzene (piperonyl butoxide) or N-(2-ethyl-heptyl)bicyclo-[2,2-1]5-heptene-2,3-dicarboximide or piperonyl-bis-2-(2'-n-butoxy-ethoxy)-ethyl acetal (tropital).

The novel method of the invention for combatting parasites such as insects, nematodes and acariens comprises contacting the parasites with a pesticidally effective amount of at least one compound of formula I.

In the following examples there are described several preferred embodiments to illustrate the invention. However, it should be understood that the invention is not intended to be limited to the specific embodiments.

EXAMPLE 1

(RS)α-cyano-3-phenoxy-benzyl (1R,cis)2,2-dimethyl-3-(1,2-propadienyl)-cyclopropane-carboxylate 2.06 g of dicyclohexylcarbodiimide were added at 0° C. to a solution of 1.52 g (1R,cis) 2,2-dimethyl-3-(1,2-propadienyl)-cyclopropane-carboxylic acid in 30 ml of methylene chloride followed by the addition of a few crystals of 4-dimethylamino-pyridine after which the mixture was stirred at 0° C. for 15 minutes. A solution of 2.47 g of (RS)α-cyano-3-phenoxy-benzyl alcohol in 10 ml of methylene chloride was added to the mixture which was stirred at 20° C. for 4 hours and was filtered. The filtrate was evaporated to dryness under reduced pressure and the residue was chromatographed over silica gel. Elution with a 3-7 benzene-petroleum ether (b.p.=35° to 70° C.) mixture and then with a 7-3 benzene-petroleum ether (b.p.=35° to 70° C.) mixture yielded 2.89 g of (RS)α-cyano-3-phenoxy-benzyl (1R,cis) 2,2-dimethyl-3-(1,2-propadienyl)-cyclopropane-carboxylate.

Analysis: $C_{23}H_{21}NO_3$; molecular weight=359.428: Calculated: %C 76.86; %H 5.89; %N 3.90; Found: %C 76.60; %H 5.90; %N 3.80

U.V. Spectrum (ethanol): Inflex. towards 230 nm: $E^{1\%}=342$; Inflex. towards 260 nm: $E^{1\%}=49$; Inflex. towards 279 nm: $D_{1cm}{}^{1\%}=53$; Max. at 278 nm: $E_{1cm}{}^{1\%}=58$

EXAMPLE 2

5-Benzyl-3-furyl-methyl (1R,cis) 2,2-dimethyl-3-(1,2-propadienyl)-cyclopropane-carboxylate 4.06 g of dicyclohexylcarbodiimide were added at 0° C. to a solution of 1.52 g of (1R,cis)2,2-dimethyl-3-(1,2-propadienyl)-cyclopropane carboxylic acid in 40 ml of methylene chloride followed by addition of a few crystals of 4-dimethylaminopyridine and stirring at 0° C. for 15 minutes. A solution of 2.07 g of 5-benzyl-3-furyl-methanol in 10 ml of methylene chloride were added at 0° C. to the mixture which was stirred at 20° C. for 4 hours and was then filtered. The filtrate was evaporated to dryness under reduced pressure and the residue was chromatographed over silica gel. Elution with a 1-1 benzene-petroleum ether (b.p.=35° to 70° C.) yielded 2.72 g of 5-benzyl-3-furyl-methyl (1R,cis)2,2-dimethyl-3-(1,2-propadienyl)-cyclopropane-carboxylate.

Analysis: $C_{21}H_{22}O_3$; molecular weight=322.407: Calculated: %C 78.23; %H 6.88; Found: %C 77.90; %H 6.70

U.V. Spectrum (ethanol): Inflex. towards 251 nm: $E_{1cm}{}^{1\%}=522$; Inflex. towards 252 nm: $E_{1cm}{}^{1\%}=10$; Max. at 258 nm: $E_{1m}{}^{1\%}=9$; Max. at 268 nm: $E_{1cm}{}^{1\%}=6$

EXAMPLE 3

5-Benzyl-3-furyl-methyl (1R,trans)2,2-dimethyl-3-(1,2-propadienyl)-cyclopropane-carboxylate 1.22 g of dicyclohexylcarbodiimide and a few crystals of 4-dimethylamino-pyridine were added at 0° C. to a solution of 900 mg of (1R,trans) 2,2-dimethyl-3-(1,2-propadienyl)cyclopropane-carboxylic acid in 20 ml of methylene chloride and the mixture was stirred at 0° C. for 15 minutes. A solution of 1.23 g of 5-benzyl-3-furyl-methanol in 7 ml of methylene chloride was added to the mixture which was stirred at 20° C. for 24 hours and was filtered. The filtrate was evaporated to dryness under reduced pressure and the residue was chromatographed over silica gel. Elution with a 3-7 petroleum ether (b.p.=35° to 70° C.)-benzene mixture and then a 7-3 petroleum ether (b.p.=35° to 70° C.)-benzene mixture yielded 825 mg of 5-benzyl-3-furyl-methyl (1R,trans) 2,2-dimethyl-3-(1,2-propadienyl)-cyclopropane-carboxylate with a specific rotation of $[\alpha]_D^{20}=-24°$ (c=0.6% in chloroform).

Analysis: $C_{21}H_{22}O_3$; molecular weight=322.407: Calculated: %C 78.23; %H 6.88; Found: %C 78.0; %H 6.9

U.V. Spectrum (ethanol): Inflex. towards 295 nm: $E_1$ $cm^{1\%}=489$; Max. at 251 nm: $E_1$ $cm^{1\%}=8.5$; Max. at 259 nm: $E_1$ $cm^{1\%}=8.4$; Max. at 268 nm: $E_1$ $cm^{1\%}=5.1$

EXAMPLE 4

(S) 3-allyl-2-methyl-4-oxo-2-cyclopenten-1-yl (1R,cis) 2,2-dimethyl-3-(1,2-propadienyl)-cyclopropane-carboxylate 13.6 g of dicyclohexylcarbodiimide and 100 mg of 4-dimethylaminopyridine were added at 0° C. to a solution of 10 g of (1R,cis) 2,2-dimethyl-3-(1,2-propadienyl)-cyclopropane-carboxylic acid and in 200 ml of methylene chloride and the mixture was stirred at 0° C. for 25 minutes. A solution of 11 g of (S) 3-allyl-2-methyl-1-hydroxy-cyclopenten-4-one in 35 ml of methylene chloride was added to the mixture which was stirred at 20° C. for 5 hours and was filtered. The filtrate was evaporated to dryness under reduced pressure and the residue was adde to 25 ml of hexane. The mixture was cooled to 0° C. and was vacuum filtered. The filtrate was evaporated to dryness under reduced pressure and the residue was chromatographed over silica gel. Elution with a 9-1 hexane-ethyl acetate mixture yielded 16.8 g of (S) 3-allyl-2-methyl-4-oxo-2-cyclopenten-1-yl (1R,cis) 2,2-dimethyl-3-(1,2-propadienyl)-cyclopropane-carboxylate with a specific rotation of $[\alpha]_D^{20}=+46°$ (c=1% in chloroform).

Analysis: $C_{18}H_{22}O_3$: milecular weight=286.37: Calculated: %C 75.50; %H 7.74; Found: %C 75.6; %H 7.9

EXAMPLE 5

(S) 2-methyl-3-allyl-4-oxo-2-cyclopenten-1-yl (1R,trans) 2,2-dimethyl-3-(1,2-propadienyl)-cyclopropane-carboxylate 1.22 g of dicyclohexylcarbodiimide and a few crystals of 4-dimethylamino-pyridine were added at 0° C. to a solution of 900 mg of (1R,trans) 2,2-dimethyl-3-(1,2-propadienyl)cyclopropane-carboxylic acid in 20 ml of methylene chloride and the mixture was stirred at 0° C. for 15 minutes. A solution of 990 mg of (S) 3-allyl-2-methyl-1-hydroxy-2-cyclopenten-4-one in 7 ml of methylene chloride was added to the mixture which was stirred at 20° C. for 24 hours and was filtered. The filtrate was evaporated to dryness under reduced pressure and the residue was chromatographed over silica gel. Elution with a 97-3 benzene-ethyl acetate mixture yield 468 mg of (S) 2-methyl-3-allyl-4-oxo-2-cyclopenten-1-yl (B 1R,trans) 2,2-dimethyl-3-(1,2-propadienyl)-cyclopropane-carboxylate with a specific rotation of $[\alpha]_D^{20}=-26°$ (c=0.5% in chloroform).

Analysis: Calculated: %C 75.50; %H 7.74; Found: %C 75.50; %H 7.80

Circular dichroism (ethanol): Max. at b 230 nm: $\Delta\epsilon=-22.9$; Max. at 315 nm: $\Delta\epsilon=+2.70$ U.V. Spectrum (ethanol): Max. at 229 nm: $E_1$ $_{cm}{}^{1\%} = 567$; Inflex. towards 280 nm: $E_1$ $_{cm}{}^{1\%} = 7$; Inflex. towards 295 nm: $E_1$ $_{cm}{}^{1\%} = 6$

EXAMPLE 6

(S)α-cyano-3-phenoxy-benzyl (1R,trans) 2,2-dimethyl-3-(1,2-propadienyl)-cyclopropane-carboxylate 1.22 g of dicyclohexylcarbodiimide and a few crystals of 4-dimethylamino-pyridine were added at 0° C. to a solution of 900 mg of (1R,trans) 2,2-dimethyl-3-(1,2-propadienyl)cyclopropane-carboxylic acid in 20 ml of methylene chloride and the mixture was stirred at 0° C. for 15 minutes. A solution of 1.46 g of (S)α-cyano-3-phenoxy-benzyl alcohol in 7 ml of methylene chloride was added to the mixture which was stirred for 5 hours at 20° C. and then filtered. The filtrate was evaporated to dryness under reduced pressure and the residue was chromatographed over silica gel. Elution with a 6-4 and then a 7-3 benzene-petroleum ether (b.p.=35° to 70° C.) mixture yielded 754 mg of (S)α-cyano-3-phenoxy-benzyl (1R,trans) 2,2-dimethyl-3-(1,2-propadienyl)-cyclopropane-carboxylate with a specific rotation of $[\alpha]_D{}^{20} = -25°$ (c=0.7% in chloroform).

Analysis: Calculated: %C 76.86; %H 5.89; %N 3.90; Found: %C 77.0; %H 5.9; %N 3.8

Circular dichroism (dioxane): Max. at 237 nm: $\Delta\epsilon = -2.8$; Max. at 283 nm: $\Delta\epsilon = +0.35$; Max. at 287 nm: $\Delta\epsilon = +0.32$ U.V. Spectrum (ethanol): Infex. towards 228 nm: $E_1$ $_{cm}{}^{1\%} = 362$; Inflex. towards 269 nm: $E_1$ $_{cm}{}^{1\%} = 50$; Inflex. towards 274 nm: $E_1$ $_{cm}{}^{1\%} = 55$; Max. at 279 nm: $E_1$ $_{cm}{}^{1\%} = 60$

EXAMPLE 7

(S)α-cyano-3-phenoxy-benzyl (1R,trans) 2,2-dimethyl-3-(3-ethoxycarbonyl 1,2-butadienyl)-cyclopropane-carboxylate STEP A: Tert.-butyl (1R,trans) 2,2-dimethyl-3-(2-methoxyethyl)-cyclopropane-carboxylate A solution of 33.6 g of potassium tert.-butylate in 450 ml of dimethylformamide was added at −60° C. to a solution of 59.75 g of tert.-butyl (1R,trans) 2,2-dimethyl-3-formylcyclopropane-carboxylate, 106.14 g of methoxymethyl triphenylphosphonium chloride and one liter of dimethylformamide and the mixture was stirred at −60° C. for 30 minutes and was poured into water. Isopropyl ether was added thereto with stirring and the decanted aqueous phase was extracted with isopropyl ether. The combined organic phases were evaporated to dryness under reduced pressure and the residue was chromatographed over silica gel. Elution with 9-1 hexane-ethyl acetate mixture yielded 49.54 g of tert.-butyl (1R,trans E+Z) 2,2-dimethyl-3-(2-methoxyethyl)-cyclopropane-carboxylate.

| NMR Spectrum Spectrum (deuterochloroform): | |
|---|---|
| 6.35–6.55 ppm | } Δε ⅔ |
| 4.43 to 4.76 ppm | |
| 5.98–6.1 ppm | } ΔZ ⅓ |
| 3.98 to 4.25 ppm | |

| NMR Spectrum Spectrum (deuterochloroform): | |
|---|---|
| OCH₃ →3.55 ppm | tert.butyl →1.46 ppm |

STEP B: Tert.-butyl (1R,trans) 2,2-dimethyl-3-formyl-cyclopropane-carboxylate

A solution of 45.26 g of the product of Step A, 50 ml of 2N sodium hydroxide solution and 450 ml of acetone was stirred for 6 hours at 20° C. and was evaporated to dryness. The residue was added to water and ether and the decanted aqueous phase was extracted with ether. The combined organic phases were evaporated to dryness under reduced pressure and the residue was chromatographed over silica gel. Elution with a 4-1 hexane-ethyl acetate mixture yielded 28.75 g of tert.-butyl (1R,trans) 2,2-dimethyl-3-formyl-cyclopropane-carboxylate.

NMR Spectrum (deuterochloroform): Peaks at 1.26-1.13-1.16 ppm (hydrogens of geminal methyls); at 1.45 ppm (hydrogens of tert.-butyl); at 9.9-9.95-10 ppm (hydrogen of —COH); at 1.66 to 2.66 ppm (hydrogens of

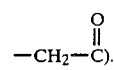

STEP C: Tert.-butyl (1R,trans) 2,2-dimethyl-3-carboxymethyl-cyclopropane-carboxylate 18 ml of 66° Bé sulfuric acid were added at 10° C. to a solution of 25.47 g of the product of Step B in 250 ml of water and after the addition of 14.47 g of potassium permanganate, the mixture was stirred at 20° C. for 2 hours. Powdered sodium bisulfite was added at 10° C. until there was a decloration of the medium and the mixture was extracted with dichloromethane. The organic phase was evaporated to dryness under reduced pressure and the residue was dissolved in ethyl acetate. The solution was extracted with aqueous sodium bicarbonate solution and the combined aqueous phases were acidified with concentrated hydrochloric acid and was extracted with dichloromethane. The organic phase was washed with water, dried and evaporated to dryness under reduced pressure to obtain 15.02 g of tert.-butyl (1R,trans) 2,2-dimethyl-3-carboxymethyl-cyclopropane-carboxylate.

NMR Spectrum (deuterochloroform): Peaks at 1.16 and 1.23 ppm (hydrogens of geminal methyls); at 1.45 ppm (hydrogens of tert.-butyl); at 1.15 to 1.76 ppm (hydrogens of cyclopropyl); at 2.08 to 2.83 ppm (hydrogens of

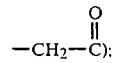

at 6.75 ppm (hydrogen of —OH-mobile).

STEP D: Tert.-butyl (1R,trans) 2,2-dimethyl-3-(2-ethoxycarbonyl-1,2-butadienyl)-cyclopropane-carboxylate A solution of 2.75 ml of triethylamine in 10 ml of dichloromethane were added to a solution of 7.14 g of 1-ethoxycarbonylethylidene triphenylphosphorane in 30 ml of dichloromethane and the mixture was stirred at 20° C. for 45 minutes to form solution A. A solution of 3.75 g of the product of Step C in 15 ml of dichloromethane was added to a solution of 2.9 ml of 1-chloro-N,N,2-trimethyl-propenylamine in 20 ml of dichloromethane and the mixture was stirred for 15 minutes at 20° C. The mixture was cooled to −20° C. and solution A was added thereto. The mixture was stirred at −20° C. for 30 minutes and was poured into water. The mixture was extracted with dichloromethane and the organic phase was evaporated to dryness under reduced pressure. The residue was chromatographed over silica gel and was eluted with a 9-1 hexane-ethyl acetate mixture to obtain 3.69 g of tert.-butyl (1R,trans) 2,2-dimethyl-3-(3-ethoxycarbonyl-1,2-butadienyl)-cyclopropane-carboxylate.

NMR Spectrum (deuterochloroform): Peaks at 1.13 to 1.41 ppm (hydrogens of geminal methyls); at 1.46 ppm (hydrogens of tert.-butyl); at 5.9 ppm (hydrogen of

=C=C—);
|
H at 1.86 to 1.91 ppm (hydrogens of CH$_3$—C=C=C); at 4.0 to 4.4 ppm (hydrogens of CH$_3$—C 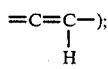 —O); at 1.13 to 1.41 ppm (hydrogens of methyl of ethoxy).

STEP E: (1R,trans) 2,2-dimethyl-3-(3-ethoxycarbonyl-1,2-butadienyl)-cyclopropane-carboxylic acid A mixture of 3.1 g of the product of Step D, 30 ml of benzene and 0.24 g of p-toluene sulfonic acid was refluxed for 30 minutes and was poured into an aqueous solution containing 0.23 g of sodium bicarbonate. The mixture was extracted with benzene and the organic phase was evaporated to dryness under reduced pressure. The residue was chromatographed over silica gel and was eluted with a 1-1 hexane-ethyl acetate mixture to obtain 1.54 g of (1R,trans) 2,2-dimethyl-3-(3-ethoxycarbonyl)-1,2-butadienyl)-cyclopropane-carboxylic acid.

NMR Spectrum (deuterochloroform): Peaks at 1.13 to 1.41 ppm (hydrogens of geminal methyls); at 1.5 to 2.16 ppm (hydrogens of cyclopropyl); at 1.86–1.91 ppm (hydrogens of CH$_3$—C=C=C); at 4.0 to 4.4 ppm (hydrogens of —CH$_2$— of ethoxy); at 1.13 to 1.41 ppm (hydrogens of CH$_3$— of ethoxy).

STEP F: (S)α-cyano-3-phenoxy-benzyl (1R,trans) 2,2-dimethyl-3-(3-ethoxycarbonyl-1,2-butadienyl)-cyclopropane-carboxylate A mixture of 1.3 g of dicyclohexylcarbodiimide and 30 mg of 4-dimethylamino-pyridine in 15 ml of dichloromethane were added to a solution of 1.5 g of the product of Step E, 1.42 g of (S)α-cyano-3-phenoxy-benzyl alcohol and 30 ml of dichloromethane and the mixture was stirred at 20° C. for 18 hours and was filtered. The filtrate was evaporated to dryness under reduced pressure and the residue was chromatographed over silica gel. Elution with a 4-1 hexane-ethyl acetate mixture yielded 1.16 g of (S)α-cyano-3-phenoxy-benzyl (1R,trans) 2,2-dimethyl-3-(3-ethoxycarbonyl-1,2-butadienyl)-cyclopropane-carboxylate with a specific rotation of $[\alpha]_D^{20} = +35°$ (chloroform).

Analysis: Calculated: %C 72.79; %H 6.11; %N 3.14; Found: %C 72.6; %H 6.0; %N 3.0

Circular dichroism (dioxane): Max. towards 232 nm: Δε= −2.3; Max. towards 283 nm: Δε= +0.86; Inflex. towards 288 nm: Δε= +0.8

U.V. Spectrum (ethanol): Inflex. towards 266 nm: $E_1 {}_{cm}{}^{1\%}$=84; Max. at 271 nm: $E_1 {}_{cm}{}^{1\%}$=85, ε=3800; Max. at 277 nm: $E_1 {}_{cm}{}^{1\%}$=86, ε=3800; Inflex. towards 296 nm: $E_1 {}_{cm}{}^{1\%}$=28

EXAMPLE 8

(1R,cis) 2,2-dimethyl-3-(1,2-propadienyl)-cyclopropane-carboxylic acid

STEP A: Methyl (1R,cis) 2,2-dimethyl-3-ethynyl-cyclopropanecarboxylate 100 ml of a solution of 1.85M of butyllithium in cyclohexane were slowly added at −100° C. to a cyclohexane solution containing 58.34 g of methyl (1R,cis) 2,2-dimethyl-3-(2,2-dibromovinyl)-cyclopropane-carboxylate and the mixture was stirred at −100° C. for 30 minutes, at −60° C. for one hour and was then poured into an iced aqueous monosodium phosphate solution. The mixture was extracted with benzene and the organic phase was evaporated to dryness under reduced pressure. The residue was rectified to obtain 14.5 g of methyl (1R,cis) 2,2-dimethyl-3-ethynyl-cyclopropane-carboxylate with a boiling point of 40° C. at 0.5 mm Hg.

NMR Spectrum (deuterochloroform): Peaks at 1.17–1.37 ppm (hydrogens of geminal methyls); at 1.72 ppm (1- and 3-hydrogens of cyclopropyl); at 2.11 ppm (ethynyl hydrogen); at 3.7 ppm (hydrogens of

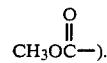

STEP B: Methyl (1R,cis) 2,2-dimethyl-3-(1,2-propadienyl)cyclopropane-carboxylate A mixture of 5.78 g of the product of Step A, 1.79 g of formaldehyde, 6.3 ml of diisopropylamine, 1.76 g of copper bromide and 60 ml of dioxane was heated at 80° C. for 18 hours and was cooled to 20° C. and diluted with water. The mixture was acidified with aqueous N hydrochloric acid and was extracted with benzene. The organic phase was filtered and evaporated to dryness under reduced pressure. The residue was chromatographed over silica gel and was eluted with a 7-3 petroleum ether (b.p.=35° to 70° C.)-benzene mixture to obtain 2,62 g of methyl (1R,cis) 2,2-dimethyl-3-(1,2-propanedienyl)-cyclopropane-carboxylate.

NMR Spectrum (deuterochloroform): Peaks at 1.17–1.25 ppm (hydrogens of geminal methyls); 1.6–1.9 ppm (hydrogens of cyclopropyl); at 3.6 ppm (hydrogens of

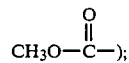

at 4.7–4.8 ppm (hydrogens of CH$_2$=); at 5.3–5.8 ppm (hydrogen of

C=C=C—).
|
H

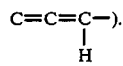

STEP C: (1R,cis) 2,2-dimethyl-3-(1,2-propadienyl)-cyclopropane-carboxylic acid A mixture of 2.56 g of the product of Step B, 20 ml of aqueous N sodium hydroxide and 40 ml of methanol was refluxed with stirring for 17 hours and was cooled to 20° C. and washed with methylene chloride. The pH of the aqueous phase was adjusted to 1 and the mixture was extracted with methylene chloride. The organic phase was evaporated to dryness under reduced pressure to obtain 2.15 g of (1R,cis) 2,2-dimethyl-3-(1,2-propadienyl)-cyclopropane-carboxylic acid with a specific rotation of $[\alpha]_D^{20} = +72°$ (c=0.5% in chloroform).

NMR Spectrum (deuterochloroform): Peaks at 1.18 and 1.25 ppm (hydrogens of geminal methyls); at 1.58 to 2.05 ppm (hydrogens of cyclopropyl); at 4.7–4.8 ppm (hydrogens of $CH_2=C=C$—); at 5.3 to 5.6 ppm (hydrogen of $CH_2=C=C-$).
|
Ⓗ

EXAMPLE 9

(1R,cis) 2,2-dimethyl-3-(1,2-propadienyl)-cyclopropane-carboxylic acid

STEP A: Tert.-butyl (1R,cis) 2,2-dimethyl-3-(1,2-propadienyl)-cyclopropane-carboxylate A mixture of 131 g of tert.-butyl (1R,cis) 2,2-dimethyl-3-ethynyl-cyclopropane-carboxylate, 32 g of paraformaldehyde, 111 ml of diisopropylamine, 31 g of copper bromide and 1,300 ml of dioxane was heated at 80° C. for 16½ hours and was cooled to 20° C. and diluted with water. The mixture was adjusted to a pH of 1 with aqueous N hydrochloric acid and was extracted with methylene chloride. The organic phase was evaporated to dryness under reduced pressure and the residue was chromatographed over silica gel. Elution with a 1-1 hexane-methylene chloride mixture yielded 44 g of tert.-butyl (1R,cis) 2,2-dimethyl-3-(1,2-propadienyl)-cyclopropane-carboxylate.

NMR Spectrum (deuterochloroform): Peaks at 1.2–1.27 ppm (hydrogens of geminal methyls); at 1.48 ppm (hydrogens of tert.-butyl); at 4.7–4.8 ppm (hydrogens of $CH_2=$); at 5.36–5.75 (hydrogens of C=C=CH—).

STEP B: (1R,cis) 2,2-dimethyl-3-(1,2-propadienyl)-cyclopropane-carboxylic acid A mixture of 82.4 g of the product of Step a and 990 ml of an ethanolic solution of N potassium hydroxide was refluxed for 16 hours, cooled to −20° C. and poured into water. The mixture was extracted with methylene chloride and the organic phase was evaporated to dryness under reduced pressure. The aqueous phase was acidified and was extracted with methylene chloride. The organic phase was washed with water and evaporated to dryness under reduced pressure. The residue was chromatographed over silica gel and was eluted with isopropyl ether to obtain 39.5 g of (1R,cis) 2,2-dimethyl-3-(1,2-propadienyl)-cyclopropane-carboxylic acid with a specific rotation of $[\alpha]_D^{20} = +86°$ (c=6.5% in chloroform).

NMR Spectrum (deuterochloroform): Peaks at 1.23–1.3 ppm (hydrogens of geminal methyls); at 1.6 to 2.05 ppm (hydrogens of cyclopropyl); at 4.7–4.9 ppm (hydrogens of $CH_2=$); at 5.3 to 6.5 ppm (hydrogen of C=C=CH—C); at 10.6 ppm (hydrogen of —COOH).

EXAMPLE 10

(1R,trans) 2,2-dimethyl-3-(1,2-propadienyl)-cyclopropane-carboxylic acid

STEP A: Tert-butyl (1R,trans) 2,2-dimethyl-3-ethynyl-cyclopropane-carboxylate 47 ml of a solution of 2.34M of butyllithium in hexane were slowly added at −100° C. to a solution of 38.7 g of tert.-butyl (1R,trans) 2,2-dimethyl-3-(2,2-dibromovinyl)-cyclopropane-carboxylate, 200 ml of ether and 200 ml of tetrahydrofuran and the mixture was stirred for 90 minutes at −80° C. and was poured into iced aqueous monosodium phosphate solution. The mixture was extracted with benzene and the organic phase was evaporated to dryness under reduced pressure. The residue was rectified under reduced pressure to obtain 9.3 g of tert.-butyl (1R,trans) 2,2-dimethyl-3-ethynyl-cyclopropane-carboxylate with a boiling point of 30° C. at 0.1 mm Hg.

NMR Spectrum (deuterochloroform): Peaks at 1.22–1.3 ppm (hydrogens of geminal methyls); at 1.47 ppm (hydrogens of tert.-butyl); at 1.57–1.65 ppm (1-hydrogen of cyclopropyl); at 1.78 to 1.96 ppm (3-hydrogen of cyclopropyl and hydrogen of ethynyl).

STEP B: Tert.-butyl (1R,trans) 2,2-dimethyl-3-(1,2-propadienyl)-cyclopropane-carboxylate A mixture of 9.2 g of the product of Step A, 2.3 g of paraformaldehyde, 8 ml of diisopropylamine, 2.3 g of copper bromide and 100 ml of dioxane was heated at 90° C. for 51 hours, was cooled to 25° C. and diluted with water. The mixture was filtered and the filtrate was extracted with benzene. The organic phase was evaporated to dryness under reduced pressure and the residue was chromatographed over silica gel. Elution with a 7-3 petroleum ether (b.p.=35° to 70° C.)-benzene yielded 3.95 g of tert.-butyl (1R,trans) 2,2-dimethyl-3-(1,2-propadienyl)-cyclopropane-carboxylate.

NMR Spectrum (deuterochloroform): Peaks at 1.13–1.23 ppm (hydrogens of geminal methyls); at 1.45 ppm (hydrogens of tert.-butyl); at 4.6 to 5.3 ppm (hydrogens of $CH_2=C=C-$).

STEP C: (1R,trans) 2,2-dimethyl-3-(1,2-propadienyl)-cyclopropane-carboxylic acid A mixture of 39 g of the product of Step B and 40 ml of toluene and 400 mg of p-toluene sulfonic acid was heated at 120° C. for 30 minutes and was cooled to 20° C. and diluted with water. The mixture was extracted with benzene and the organic phase was evaporated to dryness under reduced pressure to obtain 2.71 g of (1R,trans) 2,2-dimethyl-3-(1,2-propadienyl)-cyclopropane-carboxylic acid with a specific rotation of $[\alpha]_D^{20} = -12.5°$ (c=0.5% in chloroform).

NMR Spectrum (deuterochloroform): Peaks at 1.15–1.23 ppm (hydrogens of geminal methyls); at 1.46–1.55 ppm (1-hydrogen of cyclopropyl); at 1.97 ppm (3-hydrogen of cyclopropyl); at 4.7 to 5.3 ppm (hydrogens of propadienyl); at 10.8 ppm (hydrogen of —COOH).

EXAMPLE 11

(S)α-cyano-3-phenoxy-benzyl (1R,cis) 2,2-dimethyl-3-(3-ethoxycarbonyl-1,2-propadienyl)-cyclopropane-carboxylate

STEP A: (1R,cis) 2,2-dimethyl-3-(2-methoxy-1-ethenyl)-cyclopropane-carboxylic acid A solution of 9 g of 96.5% potassium tert.-butylate in 90 ml of dimethylformamide was added at −60° C. to a solution of 12.58 g of sodium (1R,cis) 2,2-dimethyl-3-formyl-cyclopropane-carboxylate, 350 ml of dimethylformamide and 26.27 g of methoxymethyl triphenylphosphonium chloride and the temperature was allowed to rise to 20° C. with stirring over 90 minutes. The mixture was poured into aqueous monosodium phosphate solution and was extracted with diisopropyl oxide. The combined organic phases were extracted with 100 ml of aqueous N sodium hydroxide and the aqueous extract was stirred at 5° C. with a mixture of diisopropyl oxide and monosodium phosphate. The mixture was diluted with water and the decanted aqueous phase was extracted with diisopropyl oxide. The organic phase was evaporated to dryness under reduced pressure to obtain 5.22 g of (1R,cis)(E+Z) 2,2-dimethyl-3-(2-methoxy-1-ethenyl)-cyclopropane-carboxylic acid.

NMR Spectrum (deuterochloroform):

| Peaks at | 6.4–6.6 ppm | ΔE¾ ethylenic hydrogens |
|---|---|---|
| | 4.9–5.3 ppm | |
| | 4.6–4.8 ppm | |
| | 4.7–4.9 ppm | ΔZ¼ |
| and | 6.0–6.2 ppm | | at 3.5–3.6–3.66 ppm (hydrogens of CH₃O—); at 1.13–1.21–1.28 ppm (hydrogens of geminal methyls)

STEP B: (S)α-cyano-3-phenoxy-benzyl (1R,cis) 2,2-dimethyl-3-(2-methoxy-1 (E+Z)-ethenyl)-cyclopropane-carboxylate A solution of 6.32 g of dicyclohexylcarbodiimide and 0.22 g of 4-dimethylamino-pyridine and 50 ml of dichloromethane was added at 0° C. to a solution of 5.22 g of the product of Step A, 6.9 g of (S)α-cyano-3-phenoxy-benzyl alcohol and 50 ml of dichloromethane and the mixture was stirred at room temperature for 2 hours and was filtered. The filtrate was evaporated to dryness under reduced pressure and the residue was chromatographed over silica gel. Elution with a 9-1 hexane-ethyl acetate mixture yielded 8.18 g of (S)α-cyano-3-phenoxy-benzyl (1R,cis) 2,2-dimethyl-3-(2-methoxy-1 (E+Z)-ethenyl)-cyclopropane-carboxylate.

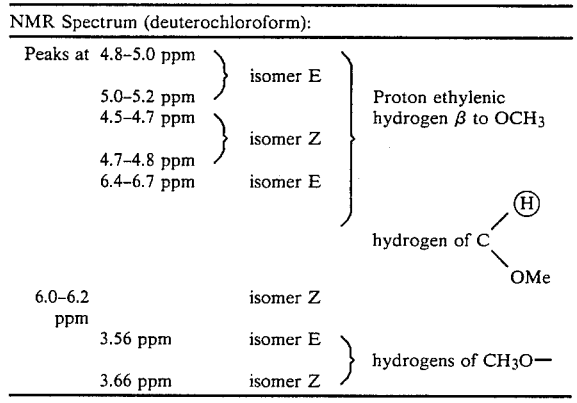

NMR Spectrum (deuterochloroform):

| Peaks at | 4.8–5.0 ppm | isomer E | Proton ethylenic hydrogen β to OCH₃ |
|---|---|---|---|
| | 5.0–5.2 ppm | | |
| | 4.5–4.7 ppm | isomer Z | |
| | 4.7–4.8 ppm | | |
| | 6.4–6.7 ppm | isomer E | |
| 6.0–6.2 ppm | | isomer Z | hydrogen of C⟨H/OMe |
| | 3.56 ppm | isomer E | hydrogens of CH₃O— |
| | 3.66 ppm | isomer Z | | at 6.4 ppm (hydrogen on carbon attached to —CN); at 1.18 to 1.25 ppm (hydrogens of geminal methyls).

STEP C: (S)α-cyano-3-phenoxy-benzyl (1R,cis) 2,2-dimethyl-3-formylmethyl-cyclopropane-carboxylate A solution of 1.9 g of the product of Step B, 20 ml of acetone and 2.5 ml of 2N hydrochloric acid solution was stirred at 20° C. for 18 hours and was evaporated to dryness under reduced pressure. The residue was added to water and the mixture was extracted with ethyl acetate. The organic phase was evaporated to dryness under reduced pressure and the residue was chromatographed over silica gel. Elution with a 4-1 hexane-ethyl acetate mixture yielded 1.3 g of (S)α-cyano-3-phenoxy-benzyl (1R,cis) 2,2-dimethyl-3-formylmethyl-cyclopropane-carboxylate.

NMR Spectrum (deuterochloroform): Peaks at 1.11 and 1.23 ppm (hydrogens of geminal methyls); at 2.85–2.96 ppm (hydrogens of

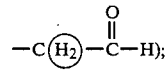

at 9.8 ppm (hydrogen of formyl); at 1.5 to 1.75 ppm (hydrogens of cyclopropyl); at 6.2 ppm (hydrogen on carbon attached to —CN); at 6.9 to 7.6 ppm (aromatic hydrogens).

STEP D: (S)α-cyano-3-phenoxy-benzyl (1R,cis) 2,2-dimethyl-3-carboxymethyl-cyclopropane-carboxylate 0.5 ml of 66° Be sulfuric acid was added dropwise at 0° C. to a mixture of 1.25 g of the product of Step C and 10 ml of water and after stirring for 5 minutes, 0.46 g of potassium permanganate were added to the mixture. The mixture was stirred for two hours while the temperature was allowed to rise to 20° C. and powdered sodium bisulfate was added thereto until decloration occured. The mixture was added to ether and sodium chloride and the mixture was extracted with ether. The organic phase was dried over sodium sulfate and evaporated to dryness under reduced pressure. The residue was chromatographed over silica gel and elution with a 1-1 hexane-ethyl acetate mixture yielded 0.98 g of (S)α-cyano-3-phenoxy-benzyl (1R,cis) 2,2-dimethyl-3-carboxymethyl-cyclopropane-carboxylate.

NMR Spectrum (deuterochloroform): Peaks at 1.16 and 1.28 ppm (hydrogens of geminal methyls); at 2.7 to 2.8 ppm (hydrogens of CH$_2$—COO); at 1.5 to 1.83 ppm (hydrogens of cyclopropyl); at 6.3 ppm (hydrogen on carbon attached to —CN); at 6.9 to 7.6 ppm (aromatic hydrogens).

STEP E: (S)α-cyano-3-phenoxy-benzyl (1R,cis) 2,2-dimethyl-3-[(3-ethoxycarbonyl) 1,2-propadienyl]-cyclopropane-carboxylate 0.62 ml of triethylamine and 5 ml of dichloromethane were added to a solution of 1.54 g of carbethoxymethylene triphenyl phosphorane in 10 ml of anhydrous dichloromethane and the mixture was stirred at 20° C. for 30 minutes to obtain solution A. A solution of 1.4 g of the product of Step D in 10 ml of dichloromethane was added to a solution of 0.65 ml of 1-chloro-N,N,2-trimethyl-propenylamine in 10 ml of dichloromethane and then solution A was added thereto at −50° C. The mixture was stirred at −50° C. for 90 minutes and was poured into water. The mixture was extracted twice with dichloromethane and the combined organic phases were evaporated to dryness under reduced pressure. The residue was chromatographed over silica gel and eluted with a 7-3 hexane-ethyl acetate mixture to obtain 0.78 g of (S)α-cyano-3-phenoxy-benzyl (1R,cis) 2,2-dimethyl-3-[(3-ethoxycarbonyl) 1,2-propadienyl]cyclopropane-carboxylate with a specific rotation of $[\alpha]_D^{20} = +40°$ (c=0.5% in chloroform).

Analysis: Calculated: %C 72.37; %H 5.84; %N 3.25; Found: %C 72.1; %H 5.9; %N 3.3

Circular dichroism (dioxane); Max. at 217 nm: Δε=+13.8; Max. at 267 nm: Δε=+0.38; Max. at 282 nm: Δε=+0.39; Inflex. towards 285 nm: Δε=+0.36

NMR Spectrum (deuterochloroform): Peaks at 1.23–1.26–1.3 ppm (hydrogens of geminal methyls and methyl of ethoxy); at 5.63 to 6.13 ppm (allenic hydrogen); at 4.05–4.16–4.28–4.4 ppm (hydrogens of —CH$_2$— of ethoxy); at 6.4 ppm (hydrogen of carbon attached to —CN).

EXAMPLE 12

(RS)-cyano-6'-phenoxy-2'-pyridyl-methyl (1R,trans) 2,2-dimethyl-3-(1,2-propadienyl)-cyclopropane-carboxylate A solution of 2.88 g of dicyclohexylcarbodiimide in 30 ml of methylene chloride was added at 0° C. to a mixture of 2 g of (1R,trans) 2,2-dimethyl-3-(1,2-propadienyl)-cyclopropane-carboxylic acid, 20 ml of methylene chloride, 2.9 g of (R.S)α-cyano-6'-phenoxy-2'-pyridyl-methanol and 100 mg of 4-dimethylamino-pyridine and the mixture was stirred at 20° C. for 16 hours and was filtered. The filtrate was evaporated to dryness under reduced pressure and the residue was chromatographed over silica gel. Elution with an 8-2 hexane-ethyl acetate mixture yielded 3.84 g of (RS)-cyano-6'-phenoxy-2'-pyridyl-methyl (1R,trans) 2,2-dimethyl-3-(1,2-propadienyl)cyclopropane-carboxylate with a specific rotation of $[\alpha]_D^{20} = -7°$ (c=1% in chloroform).

Analysis: Calculated: %C 73.31; %H 5.59; %N 7.77; Found: %C 73.2; %H 5.5; %N 7.6

Circular dichroism (dioxane): Max. at 215 nm: Δε=+3.6; Max. at 235-236 nm: Δε=−3.5; Max. at 265 nm: Δε=−0.26; Max. at 292 ppm: Δε=−0.07

EXAMPLE 13

Pentafluorobenzyl (1R,trans) 2,2-dimethyl-3-(1,2-propadienyl)cyclopropane-carboxylate A solution of 4.12 g of dicyclohexylcarbodiimide in 40 ml of methylene chloride was added at 0° C. to a mixture of 3 g of (1R,trans) 2,2-dimethyl-3-(1,2-propadienyl)-cyclopropane-carboxylic acid, 30 ml of methylene chloride, 3.96 g of pentafluorobenzyl alcohol and 100 mg of 4-dimethylaminopyridine and the mixture was stirred at 20° C. for 16 hours and was filtered. The filtrate was evaporated to dryness under reduced pressure and the residue was chromatographed over silica gel. Elution with a 9-1 hexane-ethyl acetate mixture yielded 4.78 g of pentafluorobenzyl (1R,trans) 2,2-dimethyl-3-(1,2-propadienyl)-cyclopropane-carboxylate with a specific rotation of $[\alpha]_D^{20} = -23°$ (c=0.5% in chloroform).

Circular dichroism (dioxane): Max. at 234 nm: Δε=−20.1; Max. at 266 nm: Δε=−0.05

Analysis: Calculated: %C 57.83; %H 3.94; %F 28.59; Found: %C 58.1; %H 4.1; %F 28.2

EXAMPLE 14

[1-(3-propyn-2-yl)-2,5-dioxo-imidazolidinyl]-methyl (1R,trans) 2,2-dimethyl-3-(1,2-propadienyl)-cyclopropane-carboxylate A solution of 2.88 g of dicyclohexylcarbodiimide in 30 ml of methylene chloride was added at 0° C. to a mixture of 2 g of (1R,trans) 2,2-dimethyl-3-(1,2-propadienyl)-cyclopropanecarboxylic acid, 20 ml of methylene chloride, 2.2 g of 2,5-dioxo-1-hydroxymethyl-3-(2-propynyl)-imidazole and 100 mg of 4-dimethylamino-pyridine and the mixture was stirred at 20° C. for 16 hours and was filtered. The filtrate was evaporated to dryness under reduced pressure and the residue was chromatographed over silica gel. Elution with a 1-1 hexane-ethyl acetate mixture yielded 1.6 g of [1-(3-propyn-2-yl)-2,5-dioxo-imidazolidinyl]-methyl (1R,trans) 2,2-dimethyl-3-(1,2-propadienyl)-cyclopropane-carboxylate with a specific rotation of $[\alpha]_D^{20} = -27°$ (c=1% in chloroform).

Analysis: C$_{16}$H$_{18}$N$_2$O$_4$: molecular weight=302.32: Calculated: %C 63.56; %H 6.00; %N 9.27; Found: %C 63.3; %H 6.0; %N 9.1

Circular dichroism (dioxane); Max. at 215 nm: Δε=+2.0; Max. at 235 nm: Δε=−2.8; Max. at 275 nm: Δε=+0.007; Max. at 292 nm: Δε=−0.007

EXAMPLE 15

Using the procedure of Example 1, (S)α-cyano-3-phenoxybenzyl alcohol was reacted to obtain (S)α-cyano-3-phenoxybenzyl (1R,cis) 2,2-dimethyl-3-(1,2-propadienyl)-cyclopropanecarboxylate with a specific rotation of $[\alpha]_D^{20} = +54°$ (c=0.5% in chloroform).

EXAMPLE 16

Using the procedure of Example 1, [1-(3-propyn-2-yl)-2,5-dioxo-imidazolidinyl]-methanol was reacted to obtain [1-(3-propyn-2-yl)-2,5-dioxo-imidazolidinyl] (1R,cis) 2,2-dimethyl-3-(1,2-propadienyl)-cyclopropane-carboxylate with a specific rotation of $[\alpha]_D^{20} = +14.5° \pm 2°$ (c=0.4% in chloroform).

EXAMPLE 17

Using the procedure of Example 1, pentafluoro-benzyl alcohol was reacted to obtain pentafluorobenzyl (1R,cis) 2,2-dimethyl-3-(1,2-propadienyl)-cyclopropane-carboxylate with a specific rotation of $[\alpha]_D^{20} = +20.5° \pm 1°$ (c=1.5% in chloroform).

EXAMPLE 18

Using the procedure of Example 1, (R,S)-cyano-6-phenoxy-2-pyridinyl-methanol was reacted to obtain (R,S) α-cyano-6-phenoxy-2-pyridinyl-methyl (1R,cis) 2,2-dimethyl-3-(1,2-propadienyl)-cyclopropane-carboxylate with a specific rotation of $[\alpha]_D^{20} = +59° \pm 2.5°$ (c=0.6% in chloroform).

EXAMPLE 19

Using the procedure of Example 1, (S)α-cyano-3-phenoxy-4-fluoro-benzyl alcohol was reacted to obtain (S)α-cyano-3-phenoxy-4-fluoro-benzyl (1R,cis) 2,2-dimethyl-3-(1,2-propadienyl)-cyclopropane-carboxylate with a specific rotation of $[\alpha]_D^{20} = +58° \pm 1.5°$ (c=1% in chloroform).

EXAMPLE 20

Using the procedure of Example 3, (S)α-cyano-3-phenoxy-4-fluoro-benzyl alcohol was reacted to obtain (S)α-cyano-3-phenoxy-4-fluoro-benzyl (1R,trans) 2,2-dimethyl-3-(1,2-propadienyl)-cyclopropane-carboxylate with a specific rotation of $[\alpha]_D^{20} = -19° \pm 2°$ (c=0.5% in chloroform).

EXAMPLE 21

(1R,trans) 2,2-dimethyl-3-(4-ethoxy-4-oxo-1,2-butadienyl)cyclopropane-carboxylic acid Using the procedure of Example 7, 1-ethoxycarbonylmethylene triphenylphosphorane was reacted in methylene chloride to obtain tert.-butyl (1R,trans) 2,2-dimethyl-3-(4-ethoxy-4-oxo-1,2-butadienyl)-cyclopropane-carboxylate.

NMR Spectrum (deuterochloroform): Peaks at 1.15 to 1.53 ppm (hydrogens of geminal methyls); at 1.46 ppm (hydrogens of tert.-butyl); at 5.41 to 5.83 ppm (allenic hydrogens); at 4.0 to 4.35 ppm (hydrogens of —CH₂— of ethoxy).

0.25 g of p-toluene sulfonic acid were added to a refluxing mixture of 2.5 g of the said tert.-butyl ester and 50 ml of toluene and after refluxing for 10 minutes, the mixture was evaporated to dryness under reduced pressure. The residue was chromatographed over silica gel and eluted with a 4-6 hexane-ethyl acetate mixture and 1.4 g of product is obtained.

NMR Spectrum (deuterochloroform): Peaks at 1.16 to 1.33 ppm (hydrogens of geminal methyls); at 4.05 to 4.4 ppm (hydrogens of —CH₂— of ethoxy); at 5.5 to 5.83 ppm (allenic hydrogens); at 10.4 ppm (hydrogen of —COOH).

EXAMPLE 22

A and B isomers of (S)α-cyano-3-phenoxy-benzyl (1R,trans) 2,2-dimethyl-3-(4-ethoxy-4-oxo-1,2-butadienyl)-cyclopropanecarboxylate A mixture of 2.2 g of the acid of Example 21, 25 ml of methylene chloride and 5 ml of thionyl chloride was refluxed for 2 hours and was evaporated to dryness under reduced pressure. The oil residue was taken up in benzene and the mixture was again evaporated to dryness under reduced pressure. The residue was taken up in 20 ml of benzene and 2.25 g of (S)α-cyano-3-phenoxy-benzyl alcohol were added thereto. The mixture was cooled to 10° C. and 1 ml of pyridine was added thereto. After stirring for 2 hours, the mixture was poured into N hydrochloric acid and the decanted organic phase was washed with water, dried and evaporated to dryness under reduced pressure. The residue was chromatographed over silica gel and was eluted with an 8-2 hexane-ethyl acetate mixture to obtain 0.72 g of isomer A and 0.38 g of isomer B of (S)α-cyano-3-phenoxy-benzyl (1R,trans) 2,2-dimethyl-3-(4-ethoxy-4-oxo-1,2-butadienyl)-cyclopropane-carboxylate.

NMR Spectrum (deuterochloroform): Isomer A: Peaks at 1.25 ppm (hydrogens of geminal methyls); at 5.5 to 5.83 ppm (allenic hydrogens); at 6.4 ppm (hydrogen of carbon attached to —CN); 1.15 to 1.38 ppm and 4.05 to 4.4 ppm (CH₃—CH₂—). Isomer B: Peaks at 1.22 to 1.25 ppm (hydrogens of geminal methyls); at 5.33 to 5.83 ppm (allenic hydrogens); at 6.4 ppm (hydrogen of carbon attached to —CN); at 1.18 to 1.42 ppm and 4.05 to 4.4 ppm (hydrogens of ethyl).

EXAMPLE 23

Using the procedure of Example 22, 1.5 g of (S) 3-allyl-2-metyl-1-hydroxy-2-cyclopenten-4-one were reacted to obtain 0.794 g of 3-allyl-2-methyl-4-oxo-2-cyclopenten-1-yl (1R,trans) 2,2-dimethyl-3-(4-ethoxy-4-oxo-1,2-butadienyl)-cyclopropanecarboxylate.

NMR Spectrum (deuterochloroform): Peaks at 1.23 to 1.3 ppm (hydrogens of geminal methyls); at 5.5 to 6.25 ppm (allenic hydrogens + 1-hydrogen of allethrolone); at 1.16 to 1.4 ppm and 4.03 to 4.38 ppm (hydrogens of ethyl); at 4.83 to 5.16 ppm (hydrogens of allylic —CH₂—); at 5.5 to 6.25 ppm (hydrogens of allylic —CH—).

EXAMPLE 24

Tert.-butyl (1R,cis) 2,2-dimethyl-3-[(3-ethoxycarbonyl)-1,2-propadienyl]-cyclopropane-carboxylate Using the procedure of Steps A to C of Example 7, tert.-butyl (1R,cis) 2,2-dimethyl-3-formyl-cyclopropane-carboxylate was reacted to obtain tert.-butyl (1R,cis) 2,2-dimethyl-3-carboxymethyl-cyclopropane-carboxylate which was reacted according to Step D of Example 7 with carbethoxymethyl triphenyl phosphonium bromide to obtain tert.-butyl (1R,cis) 2,2-dimethyl-3-[(3-ethoxy-carbonyl)-1,2-propadienyl]-cyclopropane-carboxylate.

NMR Spectrum (deuterochloroform): Peaks at 1.22 to 1.48 ppm (hydrogens of

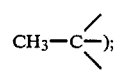

at 1.52 ppm (hydrogens of tert.-butyl); at 4.2 to 4.57 ppm (hydrogens of —CH₂— of —COOEt); at 5.45 to 6.23 ppm (ethylenic hydrogens); at 5.6–5.7 ppm (hydrogen of

EXAMPLE 25

(S)α-cyano-3-phenoxy-benzyl (1R,trans) 2,2-dimethyl-3-[(3-tert.butoxycarbonyl)-1,2-propadienyl]cyclopropane-carboxylate Using the procedure of Steps A to D of Example 11, sodium (1R,trans) 2,2-dimethyl-3-formyl-cyclopropane-carboxylate was reacted to obtain (S)α-cyano-3-phenoxy-benzyl(1R,trans) 2,2-dimethyl-3-carboxyl-methyl-cyclopropane-carboxylate which was reacted by Step E of Example 11 with 1-tert.-butoxycarbonyl-methylene triphenyl phosphorane to obtain (S)α-cyano-3-phenoxy-benzyl (1R,trans) 2,2-dimethyl-3-[(3-tert.-butoxy carbonyl)-1,2-propadienyl)-cyclopropane-carboxylate.

NMR Spectrum (deuterochloroform): Peaks at 1.05 to 1.12 ppm (hydrogens of geminal methyls); at 2.9–2.92 ppm (hydrogens of —CH$_2$—α to cyclopropyl); at 6.43 ppm (hydrogen on carbon attached to —CN).

EXAMPLE 26

Using the procedure of Step E of Example 11, 1-methoxycarbonyl-1-bromo-triphenyl phosphorane and (S)α-cyano-3-phenoxy-benzyl (1R,trans) 2,2-dimethyl-3-carboxymethyl-cyclopropane-carboxylate were reacted to obtain (S)α-cyano-3-phenoxy-benzyl (1R,trans) 2,2-dimethyl-3-(3-bromo-3-methoxycarbonyl-1,2-propadienyl)-cyclopropane-carboxylate.

NMR Spectrum (deuterochloroform): Peaks at 1.25 ppm (hydrogens of geminal methyls); at 3.83 to 3.85 ppm (hydrogens of —COOCH$_3$); at 5.63 to 5.83 ppm (allenic hydrogens); at 6.41 ppm (hydrogen on carbon attached to —CN); at 6.97 to 7.58 ppm (aromatic hydrogens).

EXAMPLE 27

(1R,trans) 2,2-dimethyl-3-(3-chloro-1,2-propadienyl)-cyclopropane-carboxylic acid

STEP A: Tert.-butyl (1R,trans) 2,2-dimethyl-3-(RS-hydroxy-2-propynyl)-cyclopropane-carboxylate A solution of ethynyl magnesium bromide was cooled to 10° C. and a solution of 15.04 g of tert.-butyl (1R,trans) 2,2-dimethyl-3-formyl-cyclopropane-carboxylate in 30 ml of tetrahydrofuran was slowly added thereto and the mixture was stirred for 2 hours and was poured into aqueous monosodium phosphate solution. The mixture was extracted with diethyl oxide and the organic phase was evaporated to dryness under reduced pressure. The oil residue was chromatographed over silica gel and was eluted with a 9-1 benzene-ethyl acetate mixture to obtain 17.17 g of tert.-butyl (1R,trans) 2,2-dimethyl-3-(RS-hydroxy-2-propynyl)-cyclopropane-carboxylate.

STEP B: Tert.-butyl (1R,trans) 2,2-dimethyl-3-(3-chloro-1,2-propadienyl)-cyclopropane-carboxylate A solution of 5.58 g of potassium tert.-butylate in 75 ml of tetrahydrofuran was added at −60° C. to a solution of 11.26 g of the product of Step A in 110 ml of tetrahydrofuran and the mixture was stirred for 25 minutes. Then, a solution of 9.4 g of tosyl chloride in 30 ml of tetrahydrofuran was slowly added thereto and after stirring for 40 minutes, 500 ml of a solution 0.5M of mixed copper-lithium chloride in tetrahydrofuran was added thereto over 45 minutes. The mixture was stirred at −60° C. for 90 minutes and was then poured into aqueous saturated ammonium chloride solution. The mixture was extracted with diethyl oxide and the combined organic phases were evaporated to dryness to obtain 19.5 g of residue. The latter was chromatographed over silica gel and was eluted with a 95-5 hexane-diisopropyl oxide to obtain 1.47 g of tert.-butyl (1R,trans) 2,2-dimethyl-3-(3-chloro-1,2-propadienyl)-cyclopropane-carboxylate.

NMR Spectrum (deuterochloroform): Peaks at 1.17 and 1.27 ppm (hydrogens of geminal methyls); at 1.46 ppm (hydrogens of tert.-butyl); at 5.38 to 5.7 ppm (hydrogen of C═C═CH); at 6.0 to 6.2 ppm (hydrogen of (C═C═CHCl).

STEP C: (1R,trans) 2,2-dimethyl-3-(3-chloro-1,2-propadienyl)cyclopropane-carboxylic acid A mixture of 1.44 g of the product of Step C, 20 ml of toluene and 0.14 g of p-toluene sulfonic acid was heated at 120° C. for 30 minutes and after the temperature returned to room temperature, the mixture was poured into aqueous sodium bicarbonate solution. The mixture was extracted with ethyl acetate and the combined organic phases were evaporated to dryness. The 1.19 g of residue was chromatographed over silica gel and was eluted with an 8-2 hexane-ethyl acetate mixture to obtain 0.64 g of (1R,trans) 2,2-dimethyl-3-(3-chloro-1,2-propadienyl)-cyclopropane-carboxylic acid.

IR Spectrum (chloroform): Absorption at 3510 cm$^{-1}$ (mono and dimer acid OH); 1730 cm$^{-1}$ shoulder and peak at 1695 cm$^{-1}$ (mono acid carbonyl); 1380 cm$^{-1}$ (geminal methyls); 1956 cm$^{-1}$ (allene).

EXAMPLE 28

Using the procedure of Example 1, 0.6 g of the acid of Step C of Example 27 and 0.73 g of (S)α-cyano-3-phenoxy-benzyl alcohol were reacted to obtain 1.0 g of (S)α-cyano-3-phenoxybenzyl (1R,trans) 2,2-dimethyl-3-(3-chloro-1,2-propadienyl)cyclopropane-carboxylate with a specific rotation of $[\alpha]_D^{20} = +26° \pm 2°$ (c=0.75% in CHCl$_3$).

EXAMPLE 29

(1R,trans) 2,2-dimethyl-3-(3-bromo-1,2-propadienyl)-cyclopropane-carboxylic acid Using the procedure of Step B of Example 27, 13.55 g of the product of Step A of Example 27 and 160 ml of a solution of 0.5M of mixed copper-lithium bromide in tetrahydrofuran were reacted to obtain 5.25 g of tert.-butyl (1R,trans) 2,2-dimethyl-3-(3-bromo-propadiene)-cyclopropane-carboxylate.

NMR Spectrum (deuterochloroform): Peaks at 1.2 and 1.27 ppm (hydrogens of geminal methyls); at 1.47 ppm (hydrogens of tert.-butyl); at 5.17 to 6.67 ppm (hydrogens of ethylenic complexes).

Using the procedure of Step C of Example 27, 6 g of the said product were reacted to obtain after chromatography over silica gel and elution with a 7-3 hexane-ethyl acetate mixture containing 0.1% acetic acid 4.1 g of (1R,trans) 2,2-dimethyl-3-(3-bromo-1,2-propadienyl)-cyclopropane-carboxylic acid.

NMR Spectrum (deuterochloroform): Peaks at 1.24 and 1.35 ppm (hydrogens of geminal methyls); at 1.59–1.67 ppm and 1.61–1.71 ppm (hydrogens of cyclopropyl α to —COO); at 5.2 to 5.75 ppm and 6.02 to 7.25 ppm (allenic hydrogens.

EXAMPLE 30

3-phenoxy-benzyl (1R,trans) 2,2-dimethyl-3-(3-bromo-1,2-propadienyl)-cyclopropane-carboxylate Using the procudure of Example 1, 1.2 g of the acid of Example 29 and 1 g of 3-phenoxy-benzyl alcohol were reacted to obtain after chromatography over silica gel and elution with a 9-1 hexane-ethyl acetate mixture 1.49 g of 3-phenoxybenzyl (1R,trans) 2,2-dimethyl-3-(3-bromo-1,2-propadienyl)-cyclopropane-carboxylate with a specific rotation of $[\alpha]_D^{20} = +15.5° \pm 2°$ (c=0.5% in chloroform).

EXAMPLE 31

Using the procedure of Example 1, 1.2 g of the acid of Example 27 and 1 g of 3-phenoxy-benzyl alcohol were reacted to obtain 3-phenoxy-benzyl (1R,trans) 2,2-dimethyl-3-(3-chloro-1,2-propadienyl)-cyclopropane-carboxylate.

EXAMPLE 32

Using the procedure of Example 1, 1.38 g of the acid of Example 29 and 0.9 g of (S) 3-allyl-2-methyl-1-hydroxy-2-cyclopenten-4-one were reduced to obtain after chromatography over silica gel and elution with a 7-3 hexane-ethyl acetate mixture 1.53 g of (S) 2-methyl-3-allyl-4-oxo-2-cyclopenten-1-yl (1R,trans) 2,2-dimethyl-3-(3-bromo-1,2-propadienyl)-cyclopropane-carboxylate with a specific rotation of $[\alpha]_D^{20} = +7.5° \pm 2°$ (c=0.5% in chloroform).

EXAMPLE 33

Using the procedure of Example 32, the acid of Example 27 was reacted to obtain (S) 2-methyl-3-allyl-4-oxo-2-cyclopenten-1-yl (1R,trans) 2,2-dimethyl-3-(3-chloro-1,2-propadienyl)-cyclopropane-carboxylate.

EXAMPLE 34

Using the procedure of Example 1, 1.2 g of the acid of Example 29 and 1.17 g of (S)α-cyano-3-phenoxy-benzyl alcohol were reacted to obtain after chromatography over silica gel and elution with a 9-1 hexane-ethyl acetate mixture and then a 8-2 hexane-isopropyl ether mixture 0.55 g of (S)α-cyano-3-phenoxy-benzyl (1R,trans) 2,2-dimethyl-3-(3-bromo-1,2-propadienyl)-cyclopropane-carboxylate melting at 98° C.

NMR Spectrum (deuterochloroform): Peaks at 1.18 and 1.25 ppm (hydrogens of geminal methyls); at 5.18 to 5.8 ppm and 6.05 to 6.25 ppm (allenic hydrogens); at 6.43 ppm (—CH—CN); at 7 to 7.67 ppm (aromatic hydrogens).

EXAMPLE 25

Methyl (1R,trans) 2,2-dimethyl-3-(3-bromo-1,2-propadienyl)-cyclopropane-carboxylate STEP A: Methyl (1R,trans) 2,2-dimethyl-3-(1RS hydroxy-propynyl)-cyclopropane-carboxylate A solution of 12.5 g of methyl (1R,trans) 2,2-dimethyl-3-formyl-cyclopropane-carboxylate in 30 ml of tetrahydrofuran was added over 15 minutes at 10° C. to a solution of ethynyl magnesium bromide and the mixture was stirred at 10° C. for 2½ hours and was poured into aqueous hydrochloric acid. The mixture was extracted with diethyloxide and the organic phase was evaporated to dryness under reduced pressure. The 15.17 g. of residue were chromatographed over silica gel and eluted with a 7-3 benzene-ethyl acetate mixture to obtain 11.74 g of methyl (1R,trans) 2,2-dimethyl-3-(1RS hydroxypropynyl)-cyclopropane-carboxylate.

STEP B: Methyl (1R,trans) 2,2-dimethyl-3-(3-bromo-1,2-propadienyl)-cyclopropane-carboxylate Using the procedure of Step B of Example 27, 3.4 g of the product of Step A were reacted with 60 ml of a solution of mixed copper-lithium bromide in tetrahydrofuran to obtain after chromatography over silica gel and elution with a 9-1 hexane-ethyl acetate mixture 1.5 g of methyl (1R,trans) 2,2-dimethyl-3-(3-bromo-1,2-propadienyl)-cyclopropane-carboxylate.

NMR Spectrum (deuterochloroform): Peaks at 1.2 and 1.29 ppm (hydrogens of geminal methyls); at 3.72 ppm (hydrogens of COOCH₃); at 1.92 to 2.15 ppm and 6.07 to 6.18 ppm (allenic hydrogens).

EXAMPLE 36

1Rtrans 2,2-dimethyl-3-(4-ethoxy-4-oxo-1,2-butadienyl) cyclopropane carboxylate of 1-(3-phenoxyphenyl) methyl (isomer A and isomer B)

By operating as in example 22, using the acid prepared in example 21 and (3-phenoxyphenyl) methyl alcohol, the product sought is isolated in the form of 2 isomers.

Isomer A: $/\alpha/_D = +107° \pm 2.5°$ (c=0.8% CHCl₃)
Isomer B: $/\alpha/_D = +108.5° \pm 3°$ (c=0.5% CHCl₃).

EXAMPLE 37

A soluble concentrate was prepared by homogenously mixing 0.25 g of the product of Example 2, 1 g of piperonyl butoxide, 0.25 g of Tween 80, 0.1 g of Topanol A and 98.4 g of water.

An emulsifiable concentrate was prepared by intimately mixing 0.015 g of the product of Example 2, 0.5 g of piperonyl butoxide, 0.1 g of Topanol A, 3.5 g of Tween 80 and 95.885 g of xylene.

A second emulsifiable concentrate was prepared by homogenously mixing 1.5 g of the product of Example 5, 20 g of Tween 80, 0.1 g of Topanol A and 78.4 g of xylene.

A fumigant composition was prepared by homogenously mixing 0.25 g of the product of Example 2, 25 g of tabu powder, 40 g of cedar needle powder, 33.75 g of pine wood powder, 0.5 g of brilliant green and 0.5 g of p-nitrophenol.

Knock-down power against houseflies 50 female houseflies 4 to 5 days old per dose were subjected to a direct spray in a Kearns and March cylinder using as the solvent a mixture of 5 volumes of acetone and 95 volumes of Isopar L (amount of solution used 2 ml per second) at concentration of 0.25 g/l. About 50 individuals per dose of treatment are used. Readings were taken every minute for 10 minutes and then at 15 minutes to determined the $KT_{50}$ by the usual method. The results are reported in Table I.

TABLE I

| Product of Example | $KT_{50}$ in min. |
|---|---|
| 1 | 3.99 |
| 2 | 2.81 |
| 3 | 4.05 |
| 4 | 3.65 |
| 5 | 3.22 |
| 6 | 4.54 |

Various modifications of the compounds and methods of the invention may be made without departing from the spirit or scope thereof and it should be understood that the invention is intended to be limited only as defined in the appended claims.

What we claim is:

1. A 3-(1,2-propadienyl)-cyclopropane-carboxylate of the formula

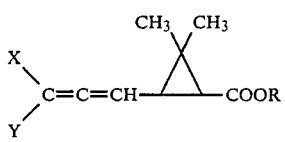

wherein R is selected from the group consisting of (1) alkyl of 1 to 18 carbon atoms, (2) benzyl optionally substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy and halogens,

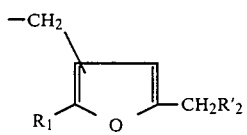

wherein $R_1$ is selected from the group consisting of hydrogen and methyl and $R_2'$ is selected from the group consisting of —C≡CH and 5-benzyl-3-furyl-methyl,

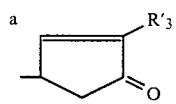

wherein a is selected from the group consisting of hydrogen and methyl and $R_3'$ is an aliphatic group of 2 to 6 carbon atoms containing at least one carbon-carbon unsaturation,

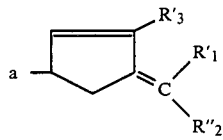

wherein a and $R_3'$ have the above definition and $R_1'$ and $R_2''$ are individually selected from the group consisting of hydrogen, halogen, alkyl of 1 to 6 carbon atoms, phenyl, cyano and alkoxy carbonyl of 2 to 5 carbon atoms,

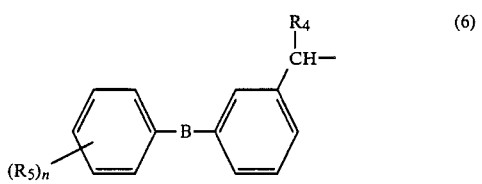

wherein B is selected from the group consisting of —CH$_2$—,

—O— and —S—, $R_4$ is selected from the group consisting of hydrogen, C≡N, —CH$_3$, —CONH$_2$, —CSNH$_2$ and —C≡CH, n is an integer from 0, 1 or 2 and $R_5$ is selected from the group consisting of halogen and —CH$_3$

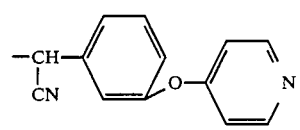

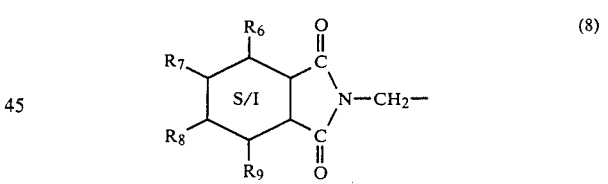

wherein $R_6$, $R_7$, $R_8$ and $R_9$ are selected from the group consisting of hydrogen, chlorine and methyl and S/I symbolizes an aromatic ring or dihydro, tetrahydro or hexahydro ring, (9) (succinimido or maleimido) —CH$_2$—

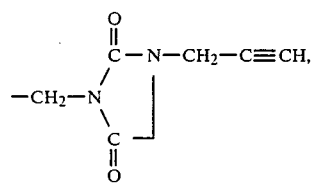

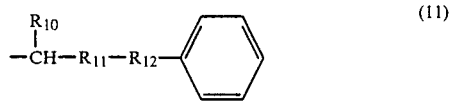

wherein $R_{10}$ is selected from the group consisting of hydrogen and —CN, $R_{12}$ is selected from the group consisting of —CH$_2$— and —O— and $R_{11}$ is selected from the group consisting of thiazolyl and thiadiazolyl with the bond to

being in any one of the positions, $R_{12}$ being bonded to $R_{11}$ by the carbon atom included between a sulfur atom and a nitrogen atom,

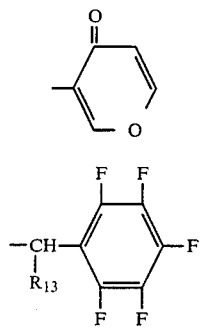

wherein $R_{13}$ is selected from the group consisting of hydrogen and —CN,

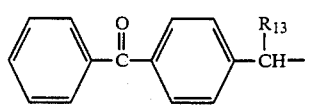

wherein $R_{13}$ has the above definition

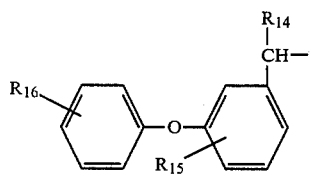

wherein $R_{14}$ is selected from the group consisting of hydrogen, methyl, ethynyl and —CN and $R_{15}$ and $R_{16}$ are individually selected from the group consisting of hydrogen, bromine and fluorine and

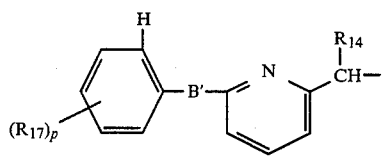

wherein $R_{14}$ has the above definition, p is 0, 1 or 2, each $R_{17}$ is selected from the group consisting of alkyl of 1 to 4 carbon atoms, alkoxy of 1 to 4 carbon atoms, alkylthio of 1 to 4 carbon atoms, alkylsulfonyl of 1 to 4 carbon atoms, —CF$_3$, 3,4-methylenedioxy, chlorine, bromine and fluorine, B' is selected from the group consisting of —O— and —S—, X and Y are both hydrogen or individually halogen or X is hydrogen or halogen and Y is alkyl of 1 to 18 carbon atoms or halogen.

2. A compound of claim 1 wherein X and Y are both hydrogen.

3. A compound of claim 1 wherein R is α-cyano-3-phenoxy-benzyl.

4. A compound of claim 1 wherein R is

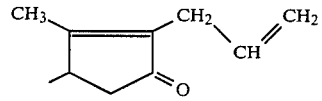

5. A compound of claim 1 wherein R is

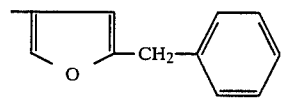

6. A compound of claim 1 wherein R is α-cyano-3-phenoxy-4-fluoro-benzyl.

7. A pesticidal composition comprising a pesticidally effective amount of at least one compound of claim 1 and an inert carrier.

8. A composition of claim 7 wherein X and Y are both hydrogen.

9. A composition of claim 7 wherein R is α-cyano-3-phenoxy-benzyl.

10. A composition of claim 7 wherein R is

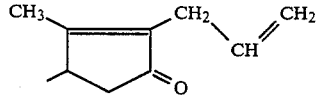

11. A composition of claim 7 wherein R is

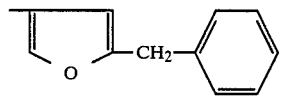

12. A composition of claim 7 wherein R is α-cyano-3-phenoxy-4-fluoro-benzyl.

13. A composition of claim 7 also containing as a second active ingredient at least one prethrinoid ester selected from the group consisting of esters of allethrolone, of 3,4,5,6-tetrahydrophthalimido-methyl alcohol, of 5-benzyl-3-furyl-methyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene methyl)-cyclopropane-1-carboxylic acids, esters of 3-phenoxy-benzyl alcohol and α-cyano-3-phenoxy-benzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxy-benzyl alcohol with 2-p-chlorophenyl-2-isopropylacetic acids, esters of allethrolones, 3,4,5,6-tetrahydrophthalimido-methyl alcohol, 5-benzyl-3-furyl-methyl alcohol, 3-phenoxy-benzyl alcohol or α-cyano-3-phenoxy-benzyl alcohols with 2,2-dimethyl-3-(1,2,2,2-tetrahaloethyl)-cyclopropane-1-carboxylic acids where halo is fluorine, chlorine or bromine wherein the compounds of formula I and the above pyrethrinoid esters are in all possible stereoisomer forms.

14. An insecticidal composition comprising an insecticidally effective amount of at least one compound of claim 1 and an inert carrier.

15. An acaricidal composition comprising an acaricidally effective amount of at least one compound of claim 1 and an inert carrier.

16. A composition for combatting affections caused by aceriens in warm-blooded animals comprising an antiacarienly effective amount of at least one compound of claim 1 and an inert carrier.

17. A nematocidal composition comprising a nematocidally effective amount of at least one compound of claim 1 and an inert carrier.

18. A method of combatting pests comprising contacting pests with a pesticidally effective amount of at least one compound of claim 1.

19. A method of claim 18 wherein X and Y are both hydrogen.

20. A method of claim 18 wherein R is α-cyano-3-phenoxy-benzyl.

21. A method of claim 18 wherein R is

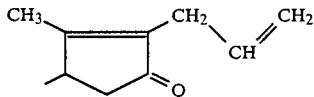

22. A method of claim 18 wherein R is

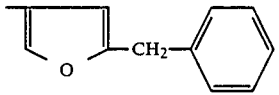

23. A method of claim 18 wherein R is α-cyano-3-phenoxy-4-fluoro-benzyl.

24. A method of claim 18 also containing as a second active ingredient at least one pyrethrinoid ester selected from the group consisting of esters of allethrolone, 3,4,5,6-tetrahydrophthalimido-methyl-alcohol, of 5-benzyl-3-furylmethyl alcohol, of 3-phenoxy-benzyl alcohol and α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene methyl)-cyclopropane-1-carboxylic acids, esters of 3-phenoxy-benzyl alcohol and α-cyano-3-phenoxybenzyl alcohols with 2,2-dimethyl-3-(2,2-dichlorovinyl)-cyclopropane-1-carboxylic acids, esters of α-cyano-3-phenoxy-benzyl alcohols with 2,2-dimethyl-3-(2,2-dibromovinyl)-cyclopropane-1-carboxylic acids, esters of 3-phenoxy-benzyl alcohol with 2-p-chlorophenyl-2-isopropyl-acetic acids, esters of allethrolones, 3,4,5,6-tetrahydrophthalimido-methyl alcohol, 5-benzyl-3-furyl-methyl alcohol, 3-phenoxy-benzyl alcohol or α-cyano-3-phenoxy-benzyl alcohols with 2,2-dimethyl-3-(1,2,2,2-tetrahaloethyl-cyclopropane-1-carboxylic acids wherein halo is fluorine, chlorine or bromine wherein the compounds of formula I and the above pyrethrinoid esters are in all possible stereoisomer forms.

25. A method of combatting insects comprising contacting insects with an insecticidally effective amount of at least one compound of claim 1.

26. A method of combatting nematodes comprising contacting nematodes with a nematocidally effective amount of at least one compound of claim 1.

27. A method of combatting acariens comprising contacting acariens with an acaricidally effective amount of at least one compound of claim 1.

28. A method of combatting infections caused by acariens in warm-blooded animals comprising contacting warm blooded animals with an anti-acarienly effective amount of at least one compound of claim 1.

* * * * *

UNITED STATES PATENT AND TRADEMARK OFFICE
CERTIFICATE OF CORRECTION

PATENT NO. : 4,537,897

DATED : Aug. 27, 1985

INVENTOR(S) : JEAN TESSIER, JEAN-PIERRE DEMOUTE and JOSEPH CADIERGUE

It is certified that error appears in the above-identified patent and that said Letters Patent is hereby corrected as shown below:

| Col. | Line | | |
|---|---|---|---|
| 9 Example 1 | 28 | "$D^{1\%}_{1CM}$" should be | -- $E^{1\%}_{1cm}$ -- |
| 22 | 3 | "2. 5g" should be | --2.25g-- |

Claim 1 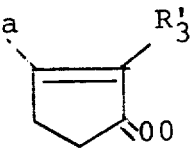

UNITED STATES PATENT AND TRADEMARK OFFICE
CERTIFICATE OF CORRECTION

PATENT NO. : 4,537,897
DATED : Aug. 27, 1985
INVENTOR(S) : Jean Tessier, Jean-Pierre Demoute and Joseph Cadiergue It is certified that error appears in the above-identified patent and that said Letters Patent is hereby corrected as shown below:

Claim 1

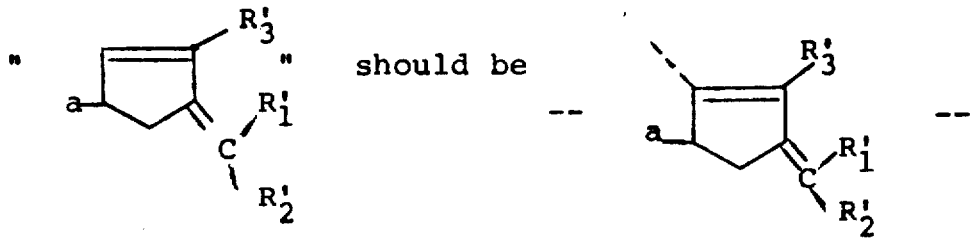

Signed and Sealed this

Eleventh Day of February 1986

[SEAL]

Attest:

DONALD J. QUIGG

Attesting Officer

Commissioner of Patents and Trademarks